US00PP21789P3

(12) United States Plant Patent
Layt

(10) Patent No.: US PP21,789 P3
(45) Date of Patent: Mar. 15, 2011

(54) ***ZOYSIA MACRANTHA* PLANT NAMED 'MAC03'**

(50) Latin Name: *Zoysia macrantha*
Varietal Denomination: MAC03

(76) Inventor: Todd Anthony Layt, Richmond (AU)

( * ) Notice: Subject to any disclaimer, the term of this patent is extended or adjusted under 35 U.S.C. 154(b) by 0 days.

(21) Appl. No.: 12/462,947

(22) Filed: Aug. 13, 2009

(65) Prior Publication Data

US 2009/0300809 P1 Dec. 3, 2009

Related U.S. Application Data

(60) Provisional application No. 61/189,875, filed on Aug. 25, 2008.

(51) Int. Cl.
*A01H 5/00* (2006.01)

(52) U.S. Cl. ..... Plt./390

(58) Field of Classification Search ..... Plt./390

See application file for complete search history.

*Primary Examiner*—Susan B McCormick Ewoldt

(57) ABSTRACT

A new and distinct cultivar of *Zoysia macrantha* plant named 'MAC03', characterized by its faster speed of growth, stronger plant density, broader leaf width, broader thickness of stolon internode and a longer stolon length.

3 Drawing Sheets

Latin name of genus and species or plant claimed:
*Zoysia macrantha.*
Variety denomination: 'MAC03'.

BACKGROUND OF THE INVENTION

The present invention relates to a new and distinct vigorous-growing perennial variety of *Zoysia macrantha,* which has been given the variety denomination of 'MAC03'. Its market class is that of a turf grass. 'MAC03' is intended for use as a lawn grass in gardening, landscaping, sports fields and amenity horticulture including coastal areas with exposure to salt.

The new *Zoysia macrantha* cultivar is a seedling selection discovered in a controlled planting of *Zoysia macrantha* wild forms, not patented. These selections were originally collected from coastal areas of NSW, Australia including Central Coast and Wollongong. The new cultivar was discovered and selected as a single plant within a population of plants of *Zoysia macrantha* designated 'T11' during summer 2006-2007 in a controlled environment at Clarendon, New South Wales, Australia. 'T11' was the result of a previous five generations of selections based on fast speed of growth and overall turf habit (strong density, rapid ground coverage) from 2000 to 2005. The result of the final selection from the 'T11' generation was greatly improved growth rates more suited to lawn use.

'MAC03' was first asexually propagated by cutting and division of stolons in 2007 in Clarendon, New South Wales, Australia. 'MAC03' has since been further asexually propagated by means of cutting and division of stolons. The distinctive characteristics of the variety have remained stable and true to type through successive cycles of asexual propagation.

SUMMARY OF THE INVENTION

The following characteristics of the new cultivar have been repeatedly observed and can be used to distinguish 'MAC03' as a new and distinct cultivar of *Zoysia macrantha* plant:

1. Fast speed of growth; and
2. Strong plant density; and
3. Medium tolerance to salt; and
4. Broad leaf width; and
5. Broad thickness of stolon internode
6. Long stolon length Plants of the new cultivar differ from plants of the *Zoysia macrantha* parent 'T11' and wild forms from coastal areas of NSW, Australia including Central Coast and Wollongong primarily in having a faster speed of growth, stronger plant density, broader leaf width, broader thickness of stolon internode and a longer stolon length.

'MAC03' is the first cultivar of the *Zoysia macrantha* species.

An application for plant breeders' rights for variety 'MAC03' has been lodged with the Australian Plant Breeders' Rights Office, and was first gazetted on 5 Oct. 2007 under Application No. 2007/275.

BRIEF DESCRIPTION OF THE PHOTOGRAPHS

The accompanying photographs show, as nearly true as it is reasonably possible to make the same in color illustrations of this type, typical foliage and growth characteristics of the new cultivar. Colors in the photographs differ slightly from the color values cited in the detailed description, which accurately describes the colors of 'MAC03'.

DETAILED BOTANICAL DESCRIPTION

Figure 1:
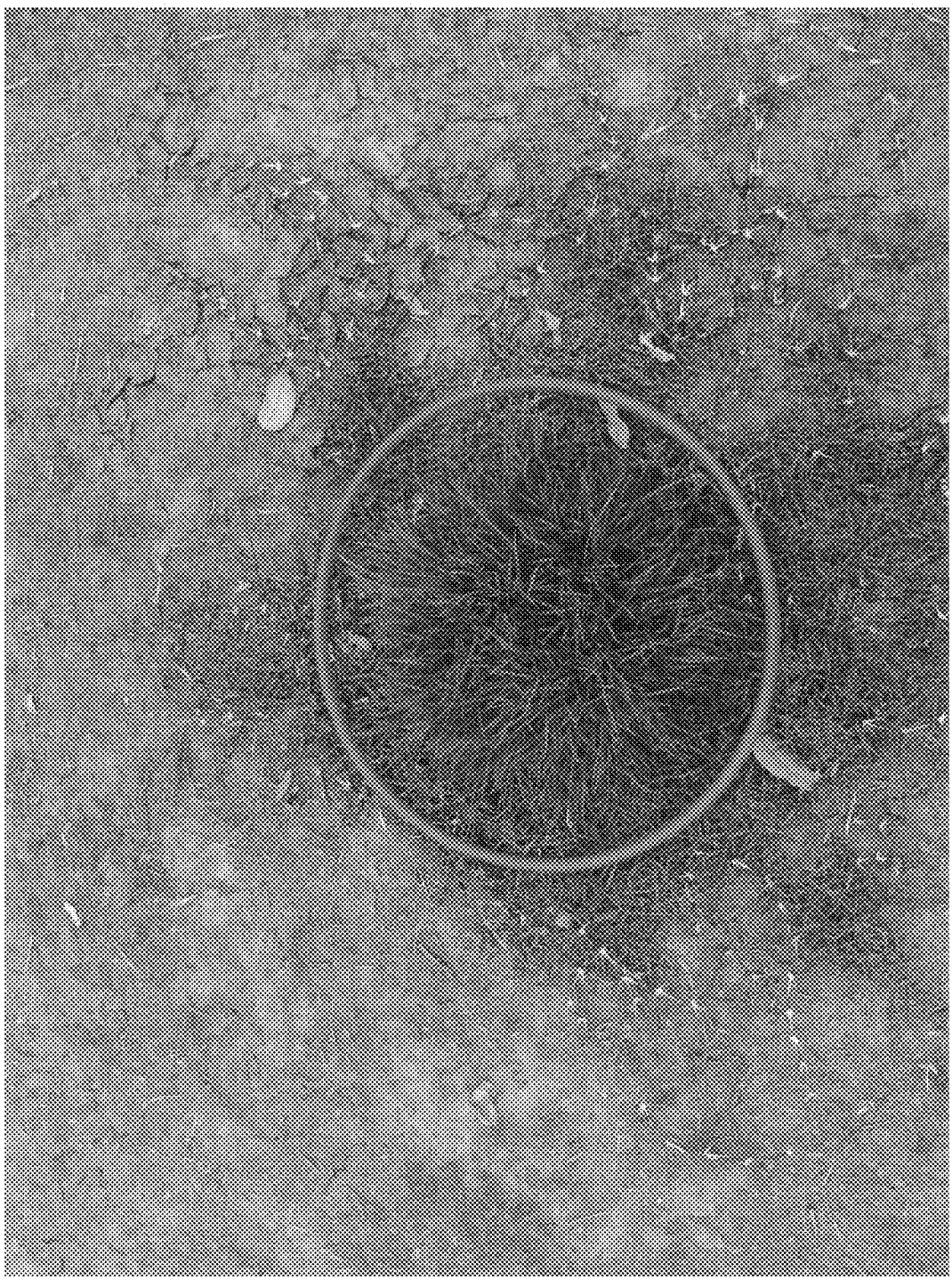
FIG. 1 illustrates a 'MAC03' plant in soil grown for approximately 14 weeks in an outdoor environment showing strong plant growth density and spread of stolons.
Figure 2:
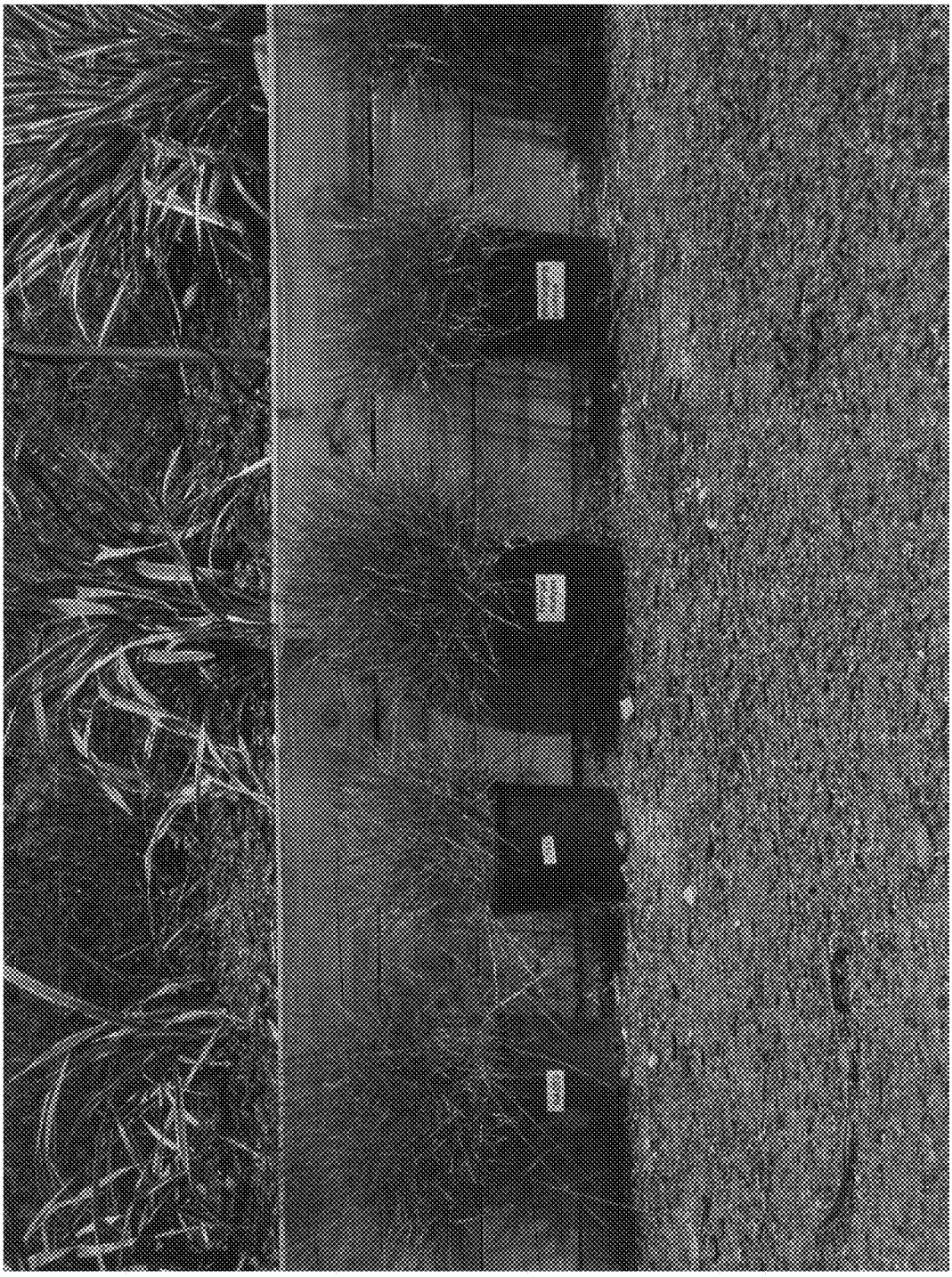
FIG. 2 illustrates the plant growth habit of a 24 week old 'MAC03' plant grown in a 200 mm pot compared to the parent 'T11' and wild forms.
Figure 3:
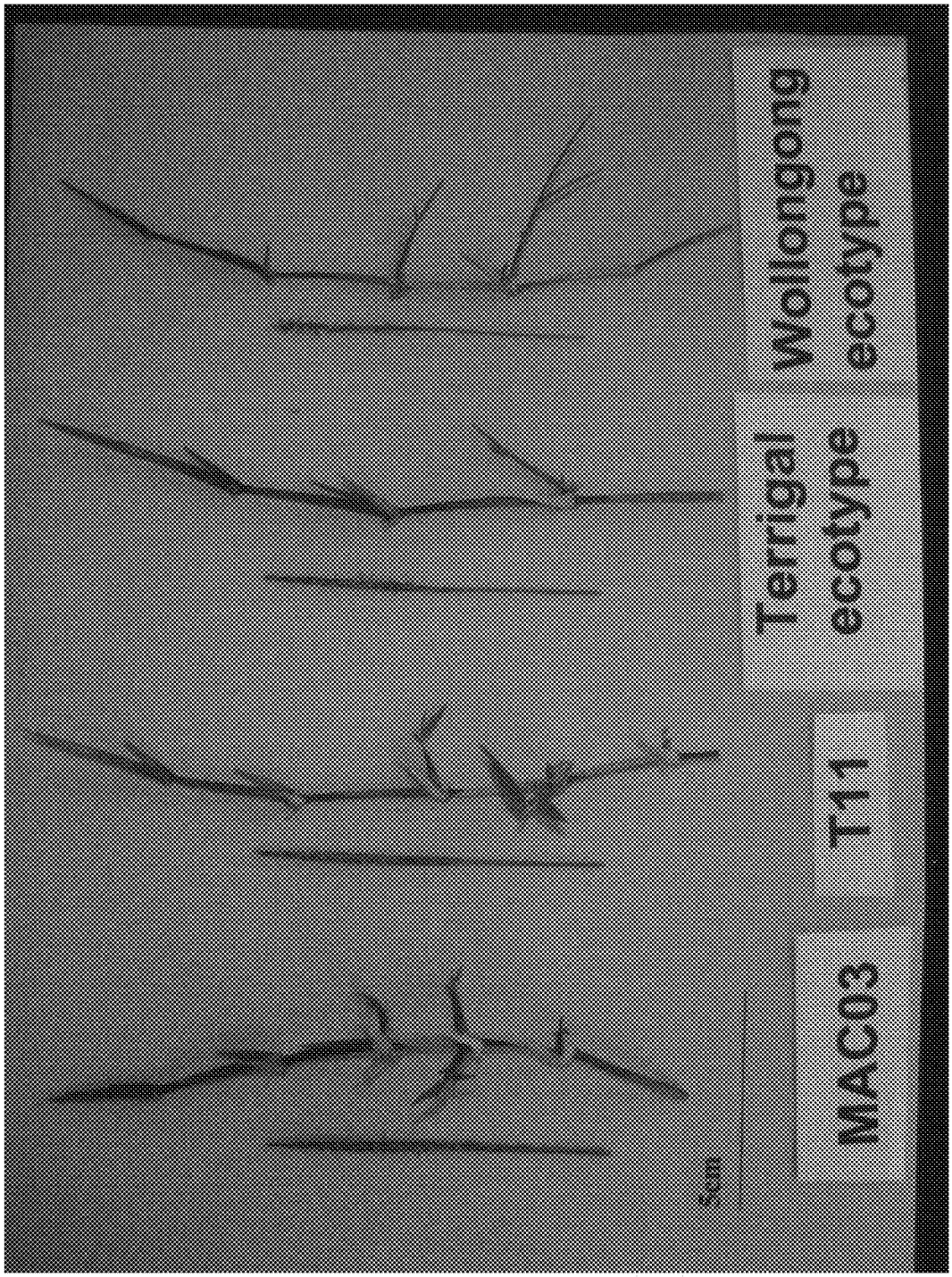
FIG. 3 illustrates 'MAC03' stolon and inflorescence detail compared to the parent 'T11' and wild forms.

The following is a detailed botanical description of a new and distinct variety of an *Zoysia macrantha* ornamental plant known as 'MAC03'. Plant observations were made on plants grown in Clarendon, New South Wales, Australia. Unless indicated otherwise, the descriptions disclosed herein are based upon observations made from February 2008 of mature 'MAC03' plants grown in nursery pots in greenhouse and outdoor growing areas with day temperature ranging from 25° C. to 35° C., night temperatures ranging from 10° C. to 15° C., and light levels ranging from 6 to 8 klux. Plants were grown for about 24 weeks with one plant per 20 cm container. Plants were trimmed 10 weeks before assessment. Those skilled in the art will appreciate that certain characteristics will vary with older or, conversely, younger plants. 'MAC03' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Zoysia macrantha* cultivar 'MAC03'.

Parentage: Parents — *Zoysia macrantha* breeder code 'T11'.

Propagation: Type — Asexual propagation of cuttings from stolons and divisions of plants.

TECHNICAL DESCRIPTION OF THE VARIETY

The description of the variety below is taken from a pot trial conducted in the Summer 2007-2008 in Clarendon, New South Wales, Australia. Plants were six-months old at the time of observation.

Plant characteristics: Vigorous-growing perennial, stoloniferous grass, culms decumbent, habit prostrate becoming erect when flowering.

Stolon: Roots at nodes, length long to very long (mean 40 cm) internode length (4th from tip) medium (mean 29 mm), diameter of internode broad (mean 2 mm), color of internode when exposed to sunlight grayed purple (RHS 187A), diameter of node medium to broad (mean 2.6 mm), branching medium, subtended by a leafy sheath with length 16 to 24 mm.

Leaf: Attachment cauline, length long (mean 96 mm), width broad (mean 3.8 mm), color of blade green (RHS 146B), leaf veins parallel and obscure, shape ligulate, cross section flat, apex narrow acute, leaf margin entire.

Ligule: Ligule is a fringe of hairs, not prominent.

Awns: Absent.

Inflorescence: Spike-like single raceme, length medium to long (mean 52 mm), color yellow green (RHS 147B).

Glumes: Predominant color grayed purple (RHS N186C), length 3-4 mm.

Lemmas: Color approximately grayed purple (RHS N186C), length 4-5 mm.

Stigma color: White (RHS 155D).

Cultural notes: 'MAC03' has been observed to survive to a cold temperature of −5° Celsius. 'MAC03' has been tested for heat tolerance to 44° Celsius and survived in Brisbane, Queensland, Australia. 'MAC03' has an average tolerance to salt in coastal conditions, typical of the species. 'MAC03' grows well in sandy loam and heavy clay soil conditions. 'MAC03' has good shade tolerance with normal growth at 50% shading. 'MAC03' competes well with invasive weeds. It produces roots well when being stolonised, and transplants well as sod.

Disease resistance: 'MAC03' has no known disease susceptibilities and is considered typical of the species for pest and disease tolerance.

COMPARISON TRIALS WITH OTHER VARIETIES

A comparative trial was carried out including 'MAC03', 'T11' (unpatented, parent), 'Terrigal ecotype' (unpatented) and 'Wollongong ecotype' (unpatented). These comparative plant selections are not commercial varieties of common use and were used in the trial as they are the nearest known plants for comparison and found in some Australian coastal ecosystems.

The results of the comparison trials are shown in Tables 1 and 2 below. In summary:

'MAC03' has stronger plant growth vigor than 'T11', 'Terrigal ecotype' and 'Wollongong ecotype'.

'MAC03' has longer stolon length than 'T11', 'Terrigal ecotype' and 'Wollongong ecotype'.

'MAC03' has a broader stolon node diameter than 'T11'.

'MAC03' has a broader stolon internode diameter than 'T11', 'Terrigal ecotype' and 'Wollongong ecotype'.

'MAC03' has a longer leaf length than 'T11', 'Terrigal ecotype' and 'Wollongong ecotype'.

'MAC03' has a broader leaf width than 'T11', 'Terrigal ecotype' and 'Wollongong ecotype'.

'MAC03' has a longer inflorescence spike than 'Wollongong ecotype'.

The comparison trials and results are described in more detail below.

The comparative trial was conducted in Clarendon, New South Wales, Australia in Spring 2007 to Summer 2007-2008. 'MAC03', 'T11', 'Terrigal ecotype' and 'Wollongong ecotype'. were compared. Individual stolons were taken from open beds, and were then planted in 200 mm pots filled with soiless potting mix. Nutrition was maintained with slow release fertilizers, which were added at the time the *Zoysia* were potted. The plants were grown in full sun in the open, with irrigation. All plants were trimmed equally 10 weeks before assessment. The pots were 24 weeks old at the time of trial. The trial design consisted of thirty pots of each variety arranged in a completely randomized design. Measurements were taken in February 2008. The results are shown in Table 1 (descriptive data) and Table 2 (statistical data) below.

TABLE 1

| Organ/Plant Part: Context | MAC03 | T11 | Terrigal ecotype | Wollongong ecotype |
|---|---|---|---|---|
| Plant: habit | stoloniferous | stoloniferous | stoloniferous | stoloniferous |
| Plant: vigour | strong to very strong | medium to strong | medium | weak to medium |

TABLE 1-continued

| Organ/Plant Part: Context | MAC03 | T11 | Terrigal ecotype | Wollongong ecotype |
|---|---|---|---|---|
| Stolon: length | long to very long | medium | medium medium | short to |
| Stolon: diameter of node | medium to broad | | medium | medium |
| Stolon: internode length | medium | medium | medium | medium |
| Stolon: internode thickness | broad | medium | medium | medium |
| Stolon: colour when exposed to sunlight | 187A | 187A | 187A | 187A |
| Leaf blade: shape | ligulate | ligulate | ligulate | ligulate |
| Leaf blade: length | long | medium to long | medium | medium |
| Leaf blade: width | broad | medium | medium | medium |
| Leaf blade: colour | 146B | 146A | 146A | 146A |
| Leaf blade: apex | narrow acute | narrow acute | narrow acute | narrow acute |
| Leaf blade: attitude | horizontal to semi-erect | horizontal to semi-erect | horizontal to semi-erect | horizontal to semi-erect |
| Leaf blade: proifle in cross-section | flat | flat | flat | flat |
| Inflorescence: lenth of spike | medium to long | medium to long | medium | medium |
| Inflorescence: length of peduncle | medium | medium | medium | medium |
| Inflorescence: anthers | present | present | present | present |
| Penduncle: colour (RHS) | 147B | 147B | 147B | 147B |
| Glume: predominant colour (RHS) | N186C | N186C | N186C | N186C |

TABLE 2

| | | | | |
|---|---|---|---|---|
| Stolon: length | | | | |
| Mean | 40.40 cm | 20.70 cm | 18.60 cm | 15.00 cm |
| Standard. Deviation | 6.50 cm | 3.50 cm | 4.00 cm | 3.00 cm |
| Lsd/signiflcance | 7.06 | P <= 0.01 | P <= 0.01 | P < = 0.01 |
| Stolon: diameter of internode | | | | |
| Mean | 1.95 mm | 1.34 mm | 1.44 mm | 1.40 mm |
| Standard. Deviation | 0.40 mm | 0.20 mm | 0.20 mm | 0.20 mm |
| Lsd/significance | 0.32 | P <= 0.01 | P <= 0.01 | P <= 0.01 |
| Stolon: diameter of node | | | | |
| Mean | 2.60 mm | 2.04 mm | 2.23 mm | 2.40 mm |
| Standard. Deviation | 0.60 mm | 0.40 mm | 0.30 mm | 0.30 mm |
| Lsd/significance | 0.48 | P <= 0.01 | ns | ns |
| Leaf blade: length | | | | |
| Mean | 96.30 mm | 6.90 mm | 43.70 mm | 53.20 mm |
| Standard. Deviation | 11.90 mm | 23.30 mm | 13.40 mm | 13.40 mm |
| Lsd/significance | 17.72 | P <= 0.01 | P <= 0.01 | P <= 0.01 |

TABLE 2-continued

| | | | | |
|---|---|---|---|---|
| Leaf blade: width | | | | |
| Mean | 3.80 mm | 12.92 mm | 12.71 mm | 3.10 mm |
| Standard. Deviation | 0.70 mm | 0.20 mm | 0.50 mm | 0.30 mm |
| Lsd/significance | 0.49 | P <= 0.01 | P <= 0.01 | P <= 0.01 |
| Inflorescence: length of spike | | | | |
| Mean | 52.20 mm | 49.90 mm | 45.50 mm | 40.10 mm |
| Standard. Deviation | 3.90 mm | 4.90 mm | 4.70 mm | 9.60 mm |
| Lsd/significance | 7.10 | ns | ns | P <= 0.01 |

where ns = not significant difference; P <= 0.01 = significant difference 1% level

What is claimed is:

1. A new and distinct cultivar of *Zoysia macrantha* plant named 'MAC03', substantially as herein shown and described.

* * * * *